United States Patent [19]
Robinson

[11] 3,972,901

[45] Aug. 3, 1976

[54] DIELS-ALDER TYPE PROCESS INVOLVING A GEMINAL-DIHALOCYCLOPROPANE AND A DIENOPHILE

[75] Inventor: Gene C. Robinson, Baton Rouge, La.

[73] Assignee: Ethyl Corporation, Richmond, Va.

[22] Filed: Jan. 18, 1971

[21] Appl. No.: 107,588

[52] U.S. Cl............................. 260/346.3; 260/165; 260/295 T; 260/326 HL; 260/346.6; 260/464; 260/468 J; 260/514 J; 260/586 C; 260/598; 260/644; 260/648 F; 260/648 R; 260/684
[51] Int. Cl.[2]...................................... C07D 307/89
[58] Field of Search............... 260/346.6, 346.3, 468

[56] References Cited
OTHER PUBLICATIONS

Robinson, J. Org. Chem., vol. 33, No. 2, Feb. 1968, pp. 607–610.
Craig et al., J.A.C.S., (1961), vol. 83, pp. 2885–2891.

*Primary Examiner*—Henry R. Jiles
*Assistant Examiner*—Bernard I. Dentz
*Attorney, Agent, or Firm*—Donald L. Johnson; John F. Sieberth

[57] ABSTRACT

Adducts containing a six-membered olefinically unsaturated ring having a halogen atom on one of the ethylenic carbon atoms (e.g., 3,5-diketo-4,8-dioxa-12-chlorotricyclo[$5.3.2.0^{2,6}$]-dodec-11-ene) are formed by heating a dienophile (e.g., maleic anhydride) with a gem-dihalocyclopropane which has at least 4 carbon atoms in the molecule and at least one hydrogen on a carbon atom singly bonded to the cyclopropane ring (e.g., 7,7-dichloro-2-oxabicyclo[4.1.0]heptane). The adducts have toxicological properties and thus may be used as insecticides, fungicides, bactericides, herbicides, miticides and the like. They are also useful in the manufacture of plasticizers, flameproofing agents, water mark detecting agents, waterproofing agents, degreasing solvents, surface active agents, and the like.

15 Claims, No Drawings

DIELS-ALDER TYPE PROCESS INVOLVING A GEMINAL-DIHALOCYCLOPROPANE AND A DIENOPHILE

This invention involves, inter alia, the discovery that by heating a gem-dihalocyclopropane having the configuration

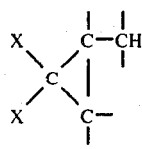

(X = halogen, i.e., F, Cl, Br, or I; preferably Cl or Br) with a dienophile to an elevated temperature, hydrogen halide and an adduct containing a six-membered olefinically unsaturated ring having a halogen atom on one of the ethylenic carbon atoms are produced. The adduct may or may not contain an additional double bond in the foregoing six-membered ring, this depending upon whether the dienophile contains olefinic or acetylenic unsaturation. Thus when the dienophile is ethylene or an ethylenic compound the adduct of the process will contain the 1-halocyclohexene configuration. On the other hand, when the dienophile is acetylene or an acetylenic compound the adduct will contain the 1-halo-1,4-cyclohexadiene configuration.

As explained in U.S. Pat. No. 3,230,237, gem-dihalocyclopropanes comprise two general types of compounds, those containing only the cyclopropane ring in the ring system and those having an additional ring fused to the cyclopropane ring (i.e., n,n-dihalobicyclo[n-3.1.0] hydrocarbon compounds). Both types are suitable for the practice of this invention provided the gem-dihalocyclopropane has at least four carbon atoms in the molecule and has at least one hydrogen atom on a carbon atom attached via a single bond to the cyclopropane ring. The disclosure of U.S. Pat. No. 3,230,237 is replete with examples of numerous illustrative gem-dihalocyclopropane compounds which meet these criteria and which accordingly are suitable for use in effecting the process of this invention. Accordingly, reference should be had to U.S. Pat. No. 3,230,237 (all disclosure of which is incorporated herein) for examples of suitable gem-dihalocyclopropane reactants for use in the present process. Although there may be differences in reactivity from compound to compound depending upon such factors as the steric configuration of the molecule, the identity of the gem-dihalo atoms and the like, it is contemplated that any gem-dihalocyclopropane having at least four carbon atoms in the molecule, at least one hydrogen atom on a carbon atom attached to the cyclopropane ring and not more than one ring fused to the cyclopropane ring may be found capable under the proper reaction conditions of undergoing the reaction of this invention. Although there are exceptions to almost any rule or generalization, the adaptability or suitability of any given gem-dihalocyclopropane as a reactant in the present process may be readily ascertained by the simple expedient of running a few pilot experiments using techniques such as those given in the Examples hereinafter.

From the standpoints of cost and ease of preparation, the use of gem-dichlorocyclopropanes meeting the foregoing structural criteria is preferred.

Particularly preferred gem-dihalocyclopropanes are those in which 1,1-dichlorocyclopropane is substituted in the ring by one or more primary or secondary alkyl groups, primary alkyl substitution being especially desirable. In addition, the ring and the alkyl group(s) or either of them may be substituted by halogen or the like.

A few exemplary gem-dihalocyclopropane reactants for the present process are 1,1-dichloro-2-methylcyclopropane; 1,1-dibromo-2-benzylcyclopropane; 1,1-diiodo-2,3-dimethylcyclopropane; 7-chloro-7-fluorobicyclo[4.1.0]heptane; 1,1-dichloro-2-isopropylcyclopropane; 2-aza-6,6-dichlorobicyclo[3.1.0]hexane; 1,1-dichloro-2-chloromethylcyclopropane; 1,1-dichloro-2-dimethoxymethylcyclopropane; cis-1,1-dichloro-2-methyl-3-allylcyclopropane; 2-methyl-3,3-dichlorotricyclo[3.2.1.0$^{2,4}$]octane; 9,9-dichlorobicyclo[6.1.0]-non-4-ene; 3-vinyl-7,7-dichlorobicyclo[4.1.0]-heptane; and the like.

Dienophiles for use in this invention are olefinic or acetylenic compounds which are capable of undergoing the Diels-Alder reaction with conjugated dienes. Such compounds are in general entirely suitable for use in practicing the process of this invention. Thus, the dienophile may be a simple unsaturated alkene such as ethylene, propylene, cis-butene-2, or the like, or it may be a simple acetylenic hydrocarbon such as acetylene, propyne, 1-heptyne, or the like. However, it is generally preferable to conduct the process of this invention utilizing dienophiles having enhanced reactivity by virtue of suitable substituents in the molecule. Among such preferred dienophiles are alkenes substituted with at least one electron-attracting group enhancing the reactivity of the ethylenic linkage, e.g., alkenes substituted with such electron-attracting groups as -COOH,

-C≡N, and the like. Another such preferred group of more reactive dienophiles is an alkyne substituted with at least one electron-attracting group enhancing the reactivity of the acetylenic linkage. Illustrative dienophiles which may be used in the practice of this invention include maleic anhydride; esters of maleic acid, such as the monomethyl ester of maleic acid, dimethyl maleate, diethyl maleate, and the like; tetracyanoethylene; crotonaldehyde; cinnamic acid (cis and trans); 1-nitropropene; acrylonitrile; acrolein; esters of acrylic acid, such as ethyl acrylate and the like; N-phenylmaleimide; esters of fumaric acid, such as dimethyl fumarate and the like; β-nitrostyrene; ethylene; tetrafluoroethylene; ketene; quinones, such as p-benzoquinone, toluquinone, and the like; citraconic anhydride; acetylenedicarboxylic acid and its esters such as its methyl and dimethyl esters and the like; acetylene; p-phenylazomaleinanil; α-acetoxyacrylonitrile; and the like. The more reactive dienophiles are, in general, those in which the carbon atoms carrying the unsaturation are flanked by one or more of the electron-attracting groups.

The particularly preferred dienophiles for use in this invention are the anhydrides and the esters of maleic acid, most especially maleic anhydride itself.

The suitability and the adaptability of any given dienophile as a reactant for the process of this invention can, if necessary, be easily ascertained by the simple expedient of performing a few pilot experiments utilizing, for example, techniques set forth in the Examples presented hereinafter.

The relative proportions of the foregoing reactants are not critical and are thus susceptible to variation. Adduct formation in accordance with this invention occurs on an equimolar (1:1) basis and thus it is generally convenient to employ the reactants in essentially equimolar quantities. However, this is not at all critical and either reactant may be in excess relative to the other.

On heating the reactants in admixture with each other to elevated temperatures hydrogen halide and the desired adduct are coproduced. Thus, in reactions occurring at ambient or mildly elevated pressures, evolution of hydrogen halide serves as a convenient index of reaction initiation. Accordingly, in effecting the process of the invention it is only necessary to raise the temperature of the reactant mixture to an elevated temperature sufficient to cause formation of hydrogen halide and the desire adduct. The temperature ranges at which these chemical transformations can be made to occur will vary to some extent depending upon such factors as the identity and reactivity of the particular gem-dihalocyclopropane reactant being used, the identity and activity of the particular dienophile reactant being utilized, and the prevailing pressure of the reaction system. In most cases the temperatures will fall within the range of from about 100° to about 250°C. although of course individual judgment will be utilized when performing any given reaction of this invention to insure that the reaction proceeds at a satisfactory reaction rate without incurring excessive thermal degradation of the desired adduct.

The reactions of this invention may be effected under any suitable reaction pressure conditions ranging from atmospheric pressure or below up to super-atmospheric pressures. As a general proposition it is desirable to conduct the reaction at either reduced or relatively mild reaction pressures as this facilitates evolution of the hydrogen halide coproduct.

In most cases the reaction proceeds very satisfactorily in the absence of a reaction diluent or solvent, however if desired, the system may include an inert diluent which is liquid under the reaction conditions being utilized. For this purpose such substances as paraffins, cycloparaffins, aromatic hydrocarbons, ethers and the like may be employed.

This invention will be still further apparent from a consideration of the following illustrative examples which are presented solely for the purposes of exemplification and which are not to be construed in any sense as imposing any limitation whatsoever upon the scope of this invention.

EXAMPLE I

Reaction of 1,1-Dichloro-2,2-dimethylcylcopropane and Maleic anhydride

To a glass tube was added maleic anhydride (73.3 mg., 0.75 mmole) and 1,1-dichloro-2,2-dimethylcyclopropane (119.3 mg., 0.86 mmole). The tube was sealed and heated at 165°–170°C. for 6–8 hours. The tube was allowed to cool and was opened (caution HCl pressure). The initially liquid product mixture crystallized with vigorous evolution of hydrogen chloride. Extraction of the crude solid (m.p. 60°–70°C.) with boiling n-hexane gave 1-chloro-2-methylcyclohexene-4,5-dicarboxylic anhydride (20.5 mg., 10 percent yield, white plates m.p. 76°–78°C.). The melting point of 1-chloro-2-methylcyclohexene-4,5-dicarboxylic anhydride as reported in the literature, J. Applied Chem. (London) 3, 145 (1953), is 79°–80°C.

Repetition at twice the scale gave 28 percent yield. Solution of a portion of the 1-chloro-2-methylcyclohexene-4,5-dicarboxylic anhydride in hot water gave the corresponding acid (m.p. 212°–216°C. sealed capillary, lit. m.p. (loc. cit.) 213°C. with decomposition).

EXAMPLE II

Reaction of 1,1-Dichloro-2-methyl-2-phenylcyclopropane with Maleic Anhydride

Into a test tube fitted with a cold finger condenser and a nitrogen bypass was put maleic anhydride (1.93 g., 19.7 mmole) and 1,1-dichloro-2-methyl-2-phenylcyclopropane (4.06 g., 20.2 mmole) along with 17.6 mg. hydroquinone. The tube containing the mixture was partially immersed in an oil bath whose temperature was slowly increased. Initial gas evolution was noted at 160°C. (bath). Steady gas evolution occurred at 178°C. with a final heating to 197°C. to insure complete reaction. Total heating time was 6 hours. The product was dissolved in benzene (5 ml.) and the solution was poured into 50 ml. n-hexane. The resultant oil soon crystallized giving 4.65 g (90 percent, m.p. 82°–90°C.) crude product which behaved as a mixture of anhydride and acid. Solution in water gave pure 1-chloro-2-phenylcyclohexene-4,5-dicarboxylic acid (m.p. 187°–189°C.).

EXAMPLE III

Reaction of 7,7-Dichloro-2-oxabicyclo[4.1.0]heptane with Maleic Anhydride

Into a test tube fitted with a cold finger was put 7,7-dichloro-2oxabicyclo[4.1.0]heptane (3.52 g., 21.1 mmole) and maleic anhydride (2.07 g., 21 mmole). The mixture was blanketed with nitrogen and heated carefully by the oil bath to 130°C. for three hours where vpc indicated slow reaction. The viscous product was only partly soluble in benzene (10 ml.). The initial extract was diluted with hexane and heated to boiling. On cooling, crystals (0.59 g., needles, m.p. 108°–110°C.) separated. Repeated benzene extraction gave an additional 1.61 g. of the crude oil which on recrystallization gave 1.09 g. crystals (total yield 1.7 g., 37 percent) of 3,5-diketo-4,8-dioxa-12-chlorotricyclo[5.3.2.0$^{2,6}$]dodec-11-ene:

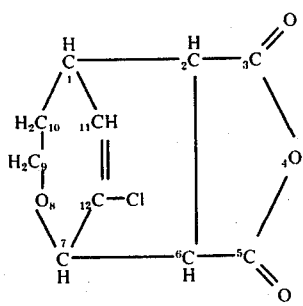

The adducts formed by the process of this invention are of use for a variety of purposes. For example, they possess useful toxicological properties and thus may be used as insecticides, fungicides, bactericides, herbicides, miticides and the like. In addition, the adducts are useful as intermediates for the manufacture of a variety of useful end products. By way of example the olefinic unsaturation present in the six-membered olefinically unsaturated ring of the adducts provides a site for halogenation and halohydrogenation reactions so that the resulting product may contain a plurality of halogen atoms in lieu of the initial ethylenic bond in the ring. This enables the synthesis of flameproofing agents, pesticides, herbicides, and the like. In addition, the halogenated cyclic hydrocarbons producible by the process of this invention can be used either directly or as intermediates for the synthesis of water mark detecting agents and degreasing solvents. Other applications for the adducts involve their use in the manufacture of plasticizers, waterproofing agents, surface active agents, and the like. Other uses for the adducts are either known to the art or will be readily apparent from a consideration of their chemical structure.

What is claimed is:

1. A process which comprises heating (i) a gem-dihalocyclopropane having (a) at least four carbon atoms in the molecule, (b) at least one hydrogen atom on a carbon atom attached to the cyclopropane ring via a single bond and (c) not more than one ring fused to the cyclopropane ring, with (ii) a dienophile to an elevated temperature within the range of from about 100° to about 250°C. sufficient to cause formation of hydrogen halide and an adduct containing a six-membered olefinically unsaturated ring having a halogen atom on one of the ethylenic carbon atoms.

2. The process of claim 1 wherein the dienophile is an alkene substituted with at least one electron-attracting group enhancing the reactivity of the ethylenic linkage.

3. The process of claim 1 wherein the dienophile is the anhydride or an ester of maleic acid.

4. The process of claim 1 wherein the dienophile is maleic anhydride.

5. The process of claim 1 wherein the dienophile is an alkyne substituted with at least one electron-attracting group enhancing the reactivity of the acetylenic linkage.

6. The process of claim 1 wherein the gem-dihalocyclopropane is a gem-dichlorocyclopropane.

7. The process of claim 1 wherein the gem-dihalocyclopropane is a gem-dichlorocyclopropane having no additional ring fused to the cyclopropane ring.

8. The process of claim 1 wherein the gem-dihalocyclopropane is a gem-dichlorocyclopropane having one additional ring fused to the cyclopropane ring.

9. The process of claim 1 wherein the gem-dihalocyclopropane is 1,1-dichlorocyclopropane substituted in the ring by at least one primary or secondary alkyl group.

10. The process of claim 1 wherein the gem-dihalocyclopropane is a gem-dichlorocyclopropane and wherein the dienophile is an alkene substituted with at least one electron-attracting group enhancing the reactivity of the ethylenic linkage.

11. The process of claim 1 wherein the gem-dihalocyclopropane is 1,1-dichlorocyclopropane substituted in the ring by a primary or secondary alkyl group and wherein the dienophile is maleic anhydride.

12. The process of claim 1 wherein the gem-dihalocyclopropane is 1,1-dichloro-2,2-dimethylcyclopropane and the dienophile is maleic anhydride whereby the adduct is 1-chloro-2-methylcyclohexene-4,5-dicarboxylic anhydride.

13. The process of claim 1 wherein the gem-dihalocyclopropane is 1,1-dichloro-2-methyl-2phenylcyclopropane and the dienophile is maleic anhydride whereby the adduct is 1-chloro-2-phenylcyclohexene-4,5-dicarboxylic anhydride.

14. The process of claim 1 wherein the gem-dihalocyclopropane is 7,7-dichloro-2oxabicyclo[4.1.0]heptane and the dienophile is maleic anhydride whereby the adduct is 3,5-diketo-4,8-dioxa-12-chloro-tricyclo[5.3.2.0$^{2,6}$]dodec-11-ene.

15. 3,5-Diketo-4,8-dioxa-12-chloro-tricyclo[5.3.2.0$^{2,6}$]-dodec-11-ene.

* * * * *